United States Patent
Li et al.

(10) Patent No.: US 12,109,322 B2
(45) Date of Patent: Oct. 8, 2024

(54) GERMICIDAL DEVICES AND APPLICATIONS OF SAME

(71) Applicant: UL Med Inc., Norcross, GA (US)

(72) Inventors: Wei Li, Norcross, GA (US); Wenwei Zhang, Norcross, GA (US); Wenting Wang, Norcross, GA (US); Yuan Di, Norcross, GA (US); Annie You, Norcross, GA (US)

(73) Assignee: UL Med Inc., Norcross, GA (US)

( * ) Notice: Subject to any disclaimer, the term of this patent is extended or adjusted under 35 U.S.C. 154(b) by 277 days.

(21) Appl. No.: 17/153,191

(22) Filed: Jan. 20, 2021

(65) Prior Publication Data
US 2021/0283285 A1   Sep. 16, 2021

Related U.S. Application Data

(60) Provisional application No. 62/990,142, filed on Mar. 16, 2020.

(51) Int. Cl.
*A61L 2/10* (2006.01)
*A61L 2/24* (2006.01)

(52) U.S. Cl.
CPC .................. *A61L 2/10* (2013.01); *A61L 2/24* (2013.01); *A61L 2202/11* (2013.01); *A61L 2202/14* (2013.01); *A61L 2202/16* (2013.01)

(58) Field of Classification Search
CPC ..... A61L 2/10; A61L 2/24; A61L 2/26; A61L 9/20; A61L 2202/11; A61L 2202/14; A61L 2202/16; A61L 2202/25; A61L 2209/111
See application file for complete search history.

(56) References Cited

U.S. PATENT DOCUMENTS 5,465,080 A * 11/1995 Liddiard ............ G08B 13/193
                                                        340/567
5,891,399 A *  4/1999 Owesen ............... A61L 9/20
                                                        422/121
(Continued)

FOREIGN PATENT DOCUMENTS

CN         2535038 Y  *  2/2003
CN         1803644 A      7/2006
(Continued)

OTHER PUBLICATIONS

Southwest Microwave, "Microwave Links", Jul. 22, 2012 (Year: 2012).*

(Continued)

*Primary Examiner* — Jennifer Wecker
*Assistant Examiner* — Brady C Pilsbury
(74) *Attorney, Agent, or Firm* — Locke Lord LLP; Tim Tingkang Xia, Esq.

(57) ABSTRACT

A germicidal device includes a lighting member operably in an on-state in which the lighting member emits ultraviolet light for killing microorganisms, or in an off-state in which the lighting member emits no light; a sensing member operably detecting at least one event occurred in an area; and a microcontroller unit coupled with the lighting member and the sensing member for controlling operations of the lighting member in a respective state in accordance with the at least one event occurred in the area. The at least one event includes a movement in the area, an acoustic wave in the area, an intrusion into the area, an expiration of an on-state time period in which the lighting member is in the on-state, an expiration of an off-state time period in which the lighting member is in the off-state, and/or an instruction from a remote operation.

18 Claims, 8 Drawing Sheets

(56) References Cited

U.S. PATENT DOCUMENTS

| | | | | |
|---|---|---|---|---|
| 6,911,177 | B2 * | 6/2005 | Deal | A61L 2/10 |
| | | | | 422/62 |
| 7,490,578 | B1 * | 2/2009 | Mottard | A01K 1/0107 |
| | | | | 422/62 |
| 2004/0051056 | A1 * | 3/2004 | Disabito | A61L 9/015 |
| | | | | 250/504 R |
| 2006/0177356 | A1 * | 8/2006 | Miller | A61L 9/20 |
| | | | | 422/121 |
| 2009/0098259 | A1 * | 4/2009 | McEllen | A23B 7/015 |
| | | | | 426/240 |
| 2012/0104027 | A1 * | 5/2012 | Hoppe | A61L 9/14 |
| | | | | 222/638 |
| 2012/0240968 | A1 * | 9/2012 | Schumacher | B08B 7/0057 |
| | | | | 134/198 |
| 2015/0090904 | A1 * | 4/2015 | Cole | A61N 5/0624 |
| | | | | 250/492.1 |
| 2017/0049915 | A1 * | 2/2017 | Brais | H05B 47/115 |
| 2017/0246331 | A1 * | 8/2017 | Lloyd | A61Q 17/04 |
| 2019/0314535 | A1 * | 10/2019 | Golkowski | A61L 2/24 |
| 2019/0321499 | A1 * | 10/2019 | Igarashi | A47K 10/48 |

FOREIGN PATENT DOCUMENTS

| | | |
|---|---|---|
| CN | 109464865 A | 3/2019 |
| KR | 20190061472 A * | 6/2019 |

OTHER PUBLICATIONS

Seeed Studio, "Microwave Sensor—5.8 GHz Doppler Radar Motion Sensor—MW0582TR11", May 8, 2011 (Year: 2011).*

* cited by examiner

GERMICIDAL DEVICES AND APPLICATIONS OF SAME

CROSS-REFERENCE TO RELATED PATENT APPLICATIONS

This application claims priority to and the benefit of U.S. Provisional Patent Application Ser. No. 62/990,142, filed Mar. 16, 2020, which is incorporated herein in its entirety by reference.

FIELD OF THE INVENTION

This invention relates generally to sterilization, and more particularly, to a novel UVC germicidal device that combines smart technology/space/surface and air sterilization functions with or without ozone.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

UVC (ultraviolet with C wavelength range) light has the effect of cracking the DNA and RNA molecular chain and kills germs and viruses in several seconds. Various germicidal devices utilize the UVC light as a core method of sterilization.

Typical germicidal devices can only be an air sterilizer or an illumination sterilizer. An air sterilizer can work during human presence but only can clean the air, not surface such as elevator buttons. An illumination sterilizer can clean surfaces but cannot work during human presence. Current UVC sterilizers may produce blind areas which cannot be cleaned by the UVC light because of the rectilinear nature of the UVC light. In addition, current products may have a basic sensor to protect humans such as a passive infrared sensor. Such sensors are limited because they cannot measure the distance between device and the person, nor distinguish between persons and other moving objects and may have the risk of miss-trigger or no-trigger in different scenarios. Various UVC and other germicidal devices on the market can produce ozone, which is harmful to the human body. Many UVC germicidal device on the market are large and heavy, limiting portability.

In addition, SARS-CoV-2 is one of most contagious and lethal viruses. The environmental factors that control replication of SARS-CoV-2 virus are still unclear. It appears that this virus has a long incubation period and can cause COVID-19 include intensified respiratory symptoms, also asymptomatic virus carry status post-infection. There is no effective treatment available at the moment. Therefore, while scientists are urged to develop specific treatment for this disease, it is also extremely important to develop products that can effectively kill the virus in our daily environment, in an affordable and smart way.

Therefore, a heretofore unaddressed need exists in the art to address the aforementioned deficiencies and inadequacies.

SUMMARY OF THE INVENTION

In one aspect, this invention relates to a germicidal device. In one embodiment, the germicidal device includes a lighting member operably in an on-state in which the lighting member emits ultraviolet (UV) light for killing microorganisms, or in an off-state in which the lighting member emits no light; a sensing member operably detecting at least one event occurred in an area; and a microcontroller unit (MCU) coupled with the lighting member and the sensing member for controlling operations of the lighting member in a respective state in accordance with the at least one event occurred in the area. In one embodiment, the at least one event includes a movement in the area, an acoustic wave in the area, an intrusion into the area, an expiration of an on-state time period in which the lighting member is in the on-state, an expiration of an off-state time period in which the lighting member is in the off-state, and/or an instruction from a remote operation. In one embodiment, the microorganisms include bacteria, fungi, viruses and/or spores.

In one embodiment, the germicidal device is configured to operate in one of:
- a default operation mode in which the lighting member is automatically in the on-state when the time is in the on-state time period, or in the off-state when the time is in the off-state time period, wherein the on-state time period and the off-state time period are predetermined;
- a manual operation mode having an on-operation and an off-operation, wherein the on-operation causes the lighting member to be in the on-state, and the off-operation causes the lighting member to be in the off-state; and
- a remote operation mode in which the lighting member is operably in one of the on-state and the off-state in response to operations of a remote control or executions of an APP of a mobile device.

In one embodiment, the germicidal device is configured such that when the lighting member is in the on-state, one of a movement in the area, an expiration of the on-state time period and a remote instruction to turn off the lighting member detected by the sensing member causes the MCU to switch the lighting member from the on-state to the off-state.

In one embodiment, the germicidal device is configured such that when the lighting member is in the off-state, an expiration of the off-state time period or a remote instruction to turn on the lighting member detected by the sensing member causes the MCU to switch the lighting member from the off-state to the on-state.

In one embodiment, the lighting member comprises a light source for emitting the UV light.

In one embodiment, the UV light has a narrow band with a wavelength range of about 10-400 nm, preferably in a ranges of about 150-280 nm. In one embodiment, the UV light has a wavelength of about 185 nm, 222 nm, 253.7 nm, or a combination of them.

In one embodiment, the light source comprises one or more UV light-emitting diodes (LEDs), or a low-pressure mercury lamp.

In one embodiment, the sensing member comprises a built-in sensor unit comprising at least one radar sensor for detecting a moving or stationary object in the area, at least one motion sensor for detecting a movement in the area, at least one acoustic sensor for detecting an acoustic wave in the area, at least one timer for timing the operation state of the lighting member, at least one temperature sensor for detecting temperature and/or temperature change of the area, or a combination of them.

In one embodiment, the at least one motion sensor comprises one or more microwave sensors, and/or one or more passive infrared (PIR) sensors.

In one embodiment, the built-in sensor unit further comprises a radio frequency (RF) receiver coupled with the MCU for operably detecting the instruction from the remote operation of the remote control.

In one embodiment, the built-in sensor unit further comprises a wireless networking module coupled with the MCU for operably detecting the instruction from the remote operation of the APP of the mobile device. In one embodiment, the wireless networking module comprises a Bluetooth® module, and/or a Wi-Fi module.

In one embodiment, the sensing member further comprises a remote sensor unit including an entrance sensor, a photo eye system, or an electric fencing system for detecting an intrusion into the area.

In one embodiment, the germicidal device further includes a power module for providing power to the lighting member, the sensing member and the MCU.

In one embodiment, the germicidal device further includes a housing surrounding the lighting member.

In one embodiment, the housing has a plurality of openings for allowing the UV light emitted from the lighting member to pass through the plurality of openings to illuminate the area.

In one embodiment, the housing comprises at least one air inlet, at least one air outlet, and at least one air pass-through channel defined between the at least one air inlet and the at least one air outlet, such that when air in the area is operably circulated through the at least one air pass-through channel, the UV light emitted from the light member kills the microorganisms in the circulated air.

In one embodiment, the housing is formed with a plurality of shutter boards that are movably jointed to each other.

In one embodiment, the germicidal device is configured to selectively operate in an illuminating mode, or in an air sterilizer mode. When the germicidal device operates in an illuminating mode, the shutter boards are moved to define a plurality of windows for allowing the UV light emitted from the lighting member to pass through the plurality of windows to illuminate the area. When the germicidal device operates in an air sterilizer mode, the shutter boards are moved to close the plurality of windows for circulating the air through the at least one air pass-through channel.

In one embodiment, the germicidal device further includes a circulating member in fluid communication with the at least one air pass-through channel for operably circulating the air through the at least one air pass-through channel. In one embodiment, the circulating member comprises one or more fans.

In another aspect, the invention relates to a method for killing microorganisms in an area with the germicidal device as disclosed above. In one embodiment, the method comprises detecting, by the sensing member, at least one event occurred in the area, wherein the at least one event includes a movement in the area, an acoustic wave in the area, an intrusion into the area, an expiration of an on-state time period in which the lighting member is in the on-state, an expiration of an off-state time period in which the lighting member is in the off-state, and/or an instruction from a remote operation; and operating, by the MCU, the lighting member in a respective state in accordance with the detected at least one event occurred in the area.

In one embodiment, the operating step comprises, when the lighting member is in the on-state, switching the lighting member from the on-state to the off-state if one of a movement in the area, an expiration of the on-state time period and a remote instruction to turn off the lighting member is detected.

In one embodiment, the operating step comprises, when the lighting member is in the off-state, switching the lighting member from the off-state to the on-state if an expiration of the off-state time period or a remote instruction to turn on the lighting member is detected.

In one embodiment, the method further comprises selectively operating the germicidal device in an illuminating mode in which the germicidal device is adapted such that the emitted UV light directly illuminates the area so as to kill the microorganisms in the illuminated area, or in an air sterilizer mode in which the germicidal device is adapted such that air in the area is circulated to pass through the emitted UV light so as to kill the microorganisms in the circulated air.

In yet another aspect, the invention relates to a non-transitory tangible computer-readable medium storing instructions which, when executed by one or more processors, cause a germicidal device to perform a method for killing microorganisms in an area. The method in one embodiment comprises detecting, by the sensing member, at least one event occurred in the area, wherein the at least one event includes a movement in the area, an acoustic wave in the area, an intrusion into the area, an expiration of an on-state time period in which the lighting member is in the on-state, an expiration of an off-state time period in which the lighting member is in the off-state, and/or an instruction from a remote operation; and operating, by the MCU, the lighting member in a respective state in accordance with the detected at least one event occurred in the area.

In one embodiment, the operating step comprises, when the lighting member is in the on-state, switching the lighting member from the on-state to the off-state if one of a movement in the area, an expiration of the on-state time period and a remote instruction to turn off the lighting member is detected.

In one embodiment, the operating step comprises, when the lighting member is in the off-state, switching the lighting member from the off-state to the on-state if an expiration of the off-state time period or a remote instruction to turn on the lighting member is detected.

In one embodiment, the method further comprises selectively operating the germicidal device in an illuminating mode in which the germicidal device is adapted such that the emitted UV light directly illuminates the area so as to kill the microorganisms in the illuminated area, or in an air sterilizer mode in which the germicidal device is adapted such that air in the area is circulated to pass through the emitted UV light so as to kill the microorganisms in the circulated air.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention.

Wherever possible, the same reference numbers are used throughout the drawings to refer to the same or like elements of an embodiment.

DETAILED DESCRIPTION OF THE INVENTION

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, the phrase at least one of A, B, and C should be construed to mean a logical (A or B or C), using a non-exclusive logical OR. As used herein, the term "and/or" includes any and all combinations of one or more of the associated listed items.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

As used herein, the terms chip or computer chip generally refers to a hardware electronic component, and may refer to or include a small electronic circuit unit, also known as an integrated circuit (IC), or a combination of electronic circuits or ICs.

As used herein, the term microcontroller unit or its acronym MCU generally refers to a small computer on a single IC chip that can carry out instructions of computer programs by performing basic arithmetic, logical, control and input/output (I/O) operations specified by the instructions for controlling other devices or machines. A microcontroller unit contains one or more central processing unit including one or more processors along with memory and programmable I/O peripherals, and is usually designed for embedded applications.

As used herein, the term system on a chip or its acronym SoC generally refers to an integrated circuit that integrates all or most components of a computer or other electronic system. These components include, but are not limited to, a central processing unit, memory, hard-disk and USB connectivity, secondary storage, input/output ports, and/or their controllers, often alongside other components such as sensing/detecting modules, power modules, and wireless modules (e.g., Wi-Fi and cellular network radio modems) on a single substrate or microchip. It may contain digital, analog, and mixed-signal processing functions.

The term interface, as used herein, generally refers to a communication tool or means at a point of interaction between components for performing wired or wireless data communication between the components. Generally, an interface may be applicable at the level of both hardware and software, and may be uni-directional or bi-directional interface. Examples of physical hardware interface may include electrical connectors, buses, ports, cables, terminals, and other I/O devices or components. The components in communication with the interface may be, for example, multiple components or peripheral devices of a computer system.

The term code, as used herein, may include software, firmware, and/or microcode, and may refer to programs, routines, functions, classes, and/or objects. Some or all code from multiple modules may be executed using a single (shared) processor. In addition, some or all code from multiple modules may be stored by a single (shared) memory. Further, some or all code from a single module may be executed using a group of processors. Moreover, some or all code from a single module may be stored using a group of memories.

The devices and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system. By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more example embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In one aspect, this invention relates to a novel ultraviolet (UV) germicidal device. The UV germicidal device utilizes short-wavelength ultraviolet (ultraviolet C or UVC) light to kill or inactivate microorganisms by destroying nucleic acids and disrupting their DNA, thereby leaving them unable to perform vital cellular functions. The UV germicidal device combines smart technology and surface, space and air sterilization functions with or without ozone. The UV germicidal device can be used in a variety of applications, such as indoor (home, dormitory, classroom) air sterilization, disinfection of elevators, cars, devices such as mobile phones and tablets, appliance such as refrigerators and washers, furniture, and food, water purification, and so on. The novel UV germicidal device, among other things, is currently commercialized under the trademark, Inoculight™.

Figure 1:
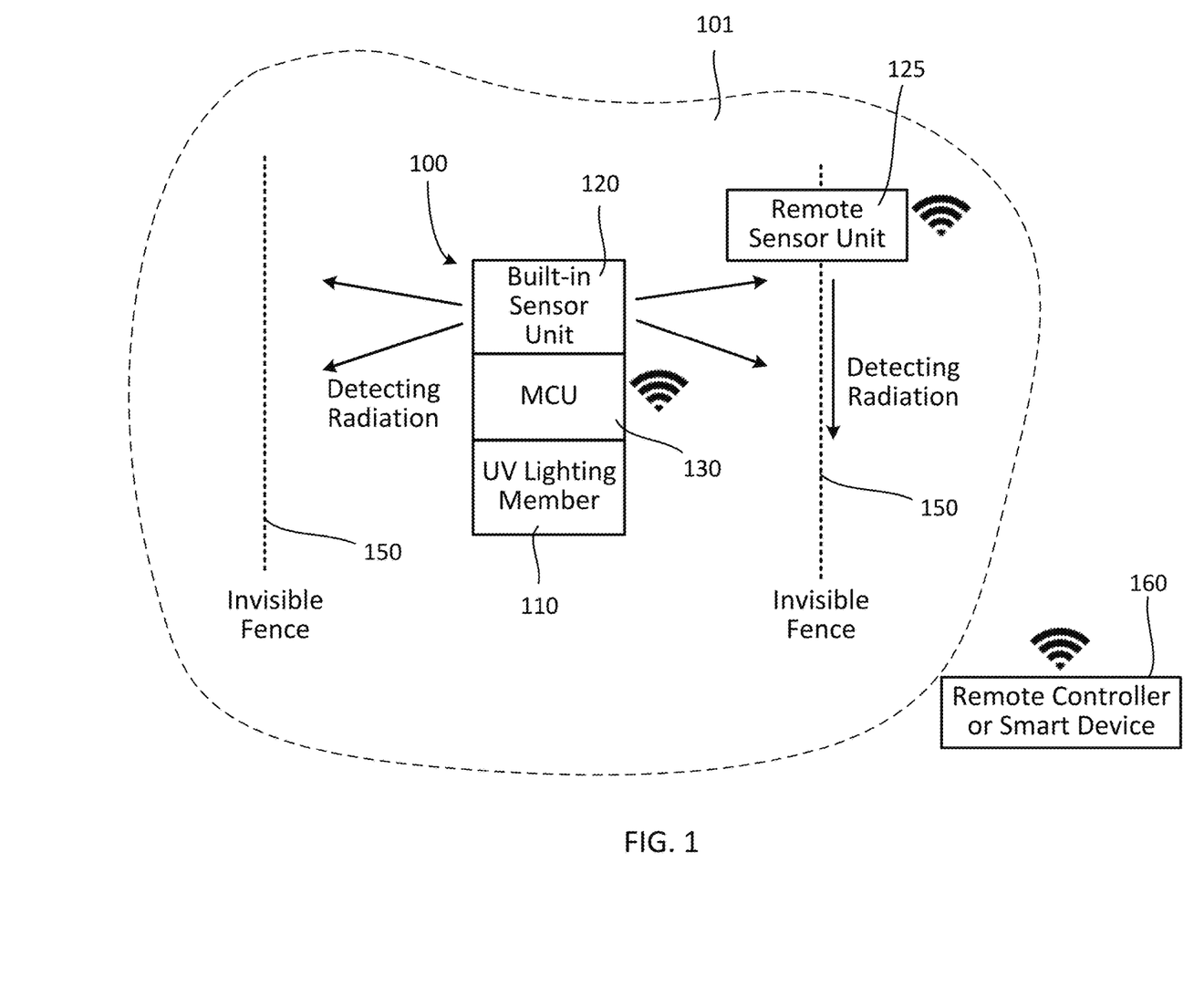
FIG. 1 shows schematically a germicidal device according to one embodiment of the invention.

Referring to FIG. 1, a germicidal device 100 is schematically shown according to one embodiment of the invention. The germicidal device 100 is placed in an area 101. The area 101 can be, but is not limited to, a room, office, hallway, or elevator. In this exemplary embodiment, the germicidal device 100 includes a lighting member 110 configured to emit UV light for killing or inactivating microorganisms, such as bacteria, fungi, viruses, spores, and/or and other pathogens, in the area 101. The UV light includes the wavelength range of about 10-400 nm, preferably about 150-280 nm. In one embodiment, the UV light has a wavelength of about 185 nm, 222 nm, 253.7 nm, or a combination of them. The UV light is used with or without addition of Ozone.

The lighting member 110 is operably in an on-state in which the lighting member 110 emits the UV light for killing or inactivating the microorganisms in the area 101, or in an off-state in which the lighting member 110 emits no light.

In some embodiments, the light source includes a low-pressure mercury lamp that utilizes low pressure ($<10^{-2}$ Pa) excited mercury vapor to emit the UV light, which has two main spectral lines: one is 253.7 nm or 222 nm wavelength; the other is 185 nm wavelength. Both spectral lines are invisible to naked eyes. The UV light of the 253.7 nm or 222 nm wavelength can sterilize surface, while the 185 nm wavelength light can ionize the air to produce ozone. The difference between these two UV light lamps is whether they produce ozone or not. Ozone is also highly oxidizing and efficient sterilization (much higher than UV efficiency), which can remedy the shortcomings of the UV light because of its rectilinear propagation creating a blind/dead spot in disinfection. However, ozone may not be suitable for certain occasions due to its smell. The two kinds of lamps are mainly different in the process of lamp materials. The ozone-free lamp is made by adding a 185 nm transmission barrier material in the lamp tube, so that the 185 nm wavelength of the UV light cannot be transmitted. Accordingly, there is no 185 nm wavelength light on the surface of the lamp tube to excite oxygen in the air, and no ozone is produced.

In some embodiments, the lighting member 110 includes a light source having one or more UV light-emitting diodes (LEDs). It should be appreciated that other types of UV light sources can also be utilized to practice the invention.

As shown in FIG. 1, the germicidal device 100 also includes a sensing member 120 and 125 for operably detecting at least one event occurred in the area 101 and a microcontroller unit (MCU) 130 coupled with the lighting member 110 and the sensing member 120 for controlling operations of the lighting member 110 in a respective state in accordance with the at least one event occurred in the area 101. In certain embodiments, the at least one event includes, but is not limited to, a movement in the area 101, an acoustic wave in the area 101, an intrusion into the area 101, an expiration of an on-state time period in which the lighting member 110 is in the on-state, an expiration of an off-state time period in which the lighting member 110 is in the off-state, and/or an instruction from a remote operation 160.

For example, when the lighting member 110 operates in the on-state, one of a movement in the area 101, an expiration of the on-state time period and a remote instruction to turn off the lighting member 110 detected by the sensing member 120 causes the MCU 130 to switch the lighting member 110 from the on-state to the off-state. When the lighting member 110 operates in the off-state, an expiration of the off-state time period or a remote instruction to turn on the lighting member 110 detected by the sensing member 120 causes the MCU 130 to switch the lighting member 110 from the off-state to the on-state.

In some embodiments, the sensing member comprises a built-in sensor unit 120. The built-in sensor unit 120 may include, but is not limited to, at least one radar sensor for detecting a moving or stationary object in the area 101, at least one motion sensor for detecting a movement in the area 101, at least one acoustic sensor for detecting an acoustic wave in the area 101, at least one timer for timing the operation state of the lighting member 110, at least one temperature sensor for detecting temperature and/or temperature change of the area 101, or a combination of them. In some embodiments, the at least one radar sensor comprises a frequency modulated continuous wave (FMCW) radar. In some embodiments, the at least one motion sensor comprises one or more microwave sensors, and/or one or more passive infrared (PIR) sensors.

In some embodiments, the built-in sensor unit 120 may further include a radio frequency (RF) receiver coupled with the MCU 130 for operably detecting the instruction from the remote operation of the remote control 160.

In one embodiment, the built-in sensor unit 120 may also have a wireless networking module coupled with the MCU 130 for operably detecting the instruction from the remote operation of the APP of the mobile device 160. In one embodiment, the wireless networking module comprises a Bluetooth® module, and/or a Wi-Fi module. The Bluetooth® module enables short-range wireless communication between the germicidal device 100 and other nearby electronic devices such as a computer, a smartphone, a television, a car, etc., nearby the germicidal device 100, while the Wi-Fi module enables the wireless connection of the germicidal device 100 to the internet.

In one embodiment, the sensing member may further include a remote sensor unit 125. The remote sensor unit 125 includes, but is not limited to, an entrance sensor, a photo eye system, or an electric fencing system for detecting an intrusion into the area 101. For example, the electric fencing system may generate an invisible electric fence 150 surrounding the germicidal device 100. When a person or animal approaches to the electric fence 150, the electric fencing system detects the intrusion of the person or animal into the area 101, which in turn, triggers the MCU 130 to turn off the lighting member 110. Similarly, the photo eye system uses infrared sensors to detect such intrusion when a person or animal approaches to the invisible infrared fence generated by the photo eye system. Also, when a person or animal enters a door of the area (room) 101, the entrance sensor can detect the entrance (i.e., intrusion), which in turn, can trigger the MCU 130 to turn off the lighting member 110.

In addition, in certain embodiments, the fence 150 can be created by a built-in sensor such as a microwave sensor, a sound sensor, or others. When operating in an illumination model, the germicidal device 100 relies on the built-in sensor or remote sensor or both to monitor human or animal movement and automatically shut off the lighting member 110, upon detection by the sensor or tripping of the fence 150.

In certain embodiments, the germicidal device 100 has three operations modes including a default operation mode, a manual operation mode and a remote operation mode.

When the germicidal device 100 operates in the default operation mode, the lighting member 110 is automatically in the on-state when the time is in the on-state time period, or in the off-state when the time is in the off-state time period. The on-state time period and the off-state time period are usually predetermined/pre-programmed. For example, the on-state time period can be set, but not limited to, from 9:00 AM to 17:00 PM when a room user is away for working, while the off-state time period is set, but not limited to, from 17:00 PM to 9:00 AM when the room user is back home. As such, the lighting member 110 is turned in the on-state and emits the UV light during 9:00 AM-17:00 PM, and the lighting member 110 is turned in the off-state and does not emit the UV light during 17:00 PM-9:00 AM. Any time during the on-state time period, when the sensing member 120 detects a movement in the area 101, an expiration of the on-state time period, or a remote instruction to turn off the lighting member 110, the MCU 130 switches the lighting member 110 from the on-state to the off-state. Similarly, any time during the off-state time period, when the sensing member 120 detects an expiration of the off-state time period, or a remote instruction to turn on the lighting member 110, the MCU 130 switches the lighting member 110 from the off-state to the on-state. It should be appreciated that the on-state time period and the off-state time period can be set in other forms, such as in multiple durations.

When the germicidal device 100 is in the remote operation mode remotely operated by a remote control and/or a mobile device 160, the lighting member 110 is operably in one of the on-state and the off-state in response to operations of the remote control 160 or executions of an APP of the mobile device 160. Similarly, any time during the on-state time period, when the sensing member 120 detects a movement in the area 101 or a remote instruction to turn off the lighting member 110, the MCU 130 switches the lighting member 110 from the on-state to the off-state, and any time during the off-state time period, when the sensing member 120 detects a remote instruction to turn on the lighting member 110, the MCU 130 switches the lighting member 110 from the off-state to the on-state. The remote operation mode can avoid UV light exposure to the user when operating.

When the germicidal device 100 operates in the manual operation mode having an on-operation and an off-operation, a user can initiate the on-operation to turn the lighting member 110 in the on-state to emit the UV light, and the user can also initiate the off-operation, when the lighting member 110 is in the on-state, to turn the lighting member 110 in the off-state in which no light is emitted.

In one embodiment, the remote operation overrides the default operation, and the manual operation overrides both of the default operation and the remote operation. For example, when the germicidal device 100 is in the default operation mode, a user can remotely turn the lighting member 110 from the on-state to the off-state, or from the off-state to the on-state. When the germicidal device 100 is in the default operation mode or the remote operation mode, a user can manually turn the lighting member 110 from the on-state to the off-state, or from the off-state to the on-state.

In another embodiment, the manual operation overrides the default operation, and the remote operation overrides both of the default operation and the manual operation. For example, when the germicidal device 100 is in the default operation mode, a user can manually turn the lighting member 110 from the on-state to the off-state, or from the off-state to the on-state. When the germicidal device 100 is in the default operation mode or the manual operation mode, a user can remotely turn the lighting member 110 from the on-state to the off-state, or from the off-state to the on-state.

Figure 2:
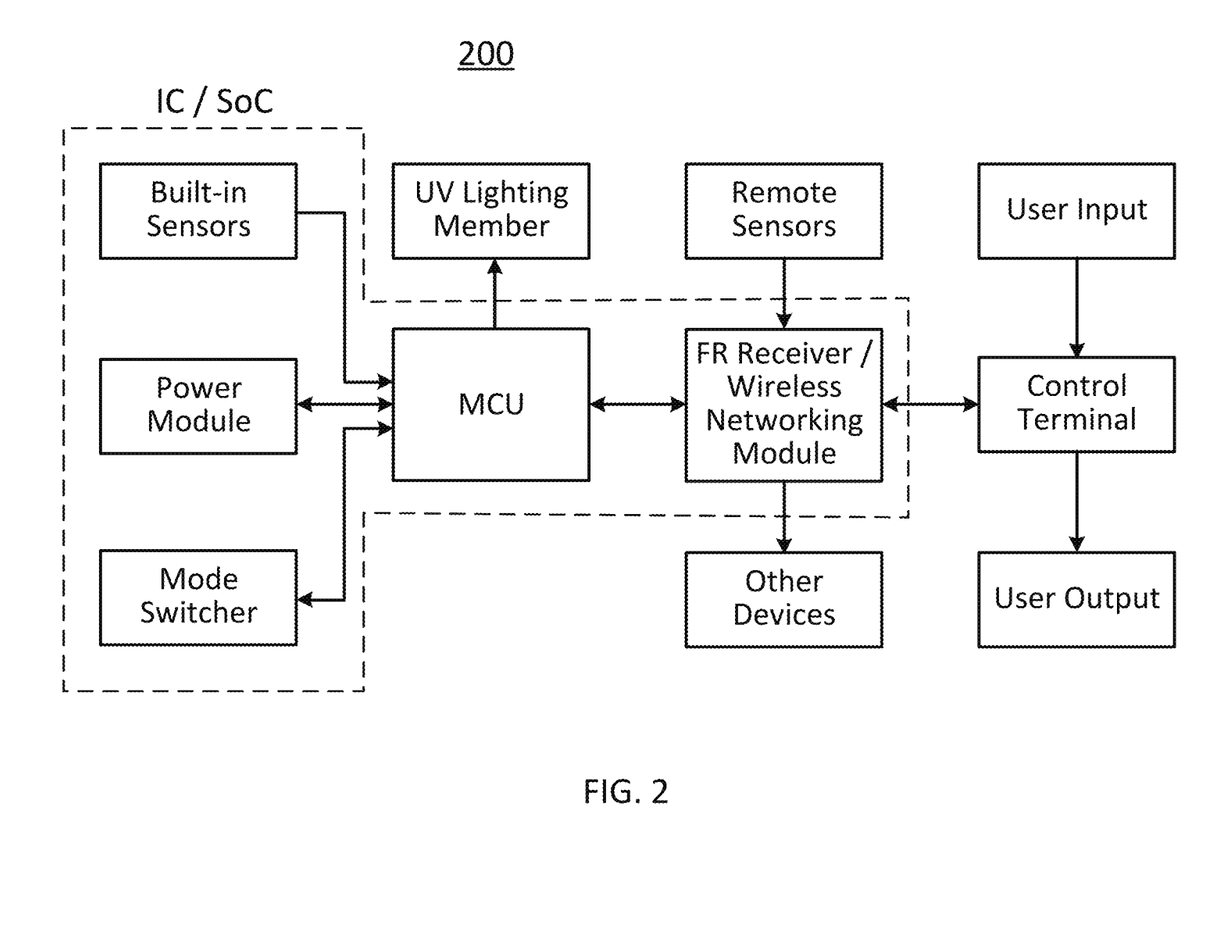
FIG. 2 shows schematically a germicidal device according to another embodiment of the invention.

Referring to FIG. 2, a germicidal device 200 is schematically shown according to another embodiment of the invention. Similar to the germicidal device 100 shown in FIG. 1, the germicidal device 200 includes an UV lighting member, a sensing member including built-in sensors and remote sensors, an RF receiver, a wireless networking module and an MCU.

The germicidal device also includes a power module coupled with the MCU for providing power to the lighting member, the sensing member and the MCU. The power module may comprise a power driver circuit and a battery coupled to the power driver circuit. The battery may be a rechargeable battery. In this case, the power module further comprises a wireless charging module coupled to the power driver circuit for wirelessly charging the rechargeable battery.

The germicidal device may further include a model switch coupled to the MCU for switching the operation modes of the germicidal device.

In certain embodiments, some or all of the built-in sensors, the power module, the model switch, the RF receiver, the wireless networking module and the MCU are integrated into a system on chip (SoC), or a single integrated circuit (IC), or two or more ICs. In certain embodiments, the wireless networking module such as the Wi-Fi module and/or the Bluetooth® module may include its own controller, which is coupled to the MCU. The MCU in certain embodiments is configured to control the operations of the germicidal device.

The operations and functions of the germicidal device 200 are similar to that of the germicidal device 100. (1) Sensor responses: the sensor member (built-in and remote sensor) collects information and sends it to the MCU. The MCU commands the power module or the mode switcher to change the operation state or shut down. At the same time, the MCU can send data to a network and the cloud via the wireless networking module. Other devices in the same network can read the data and do the response actions like shut down itself if in the same room. The terminal can receive the data, too, though the Internet/Wi-Fi. The terminal can be a smartphone, a personal computer (PC), an IPC (industrial PC), or the likes. The processing center can inform the user or administrator of the device's operations or ask the user to perform the operations. (2) Automatic run based on the user input, e.g., a space type such as an elevator or a bathroom, etc., the area size, and so on. The terminal can transfer such input into operation parameters informing the sensor and the MCU about optimal run-time and logic model or an electric fence range, etc. (3) Remote and central control: the user can remotely control the device (start-up, shutdown, and modes) via the network. (4) Remote monitoring: the user or monitor software can monitor the device via the network, and provide information on the running status, the remaining lifetime, and other statistics (big data). (5) Remote sensors network: the remote sensors can join in the network and send the data such as motion detection to the network. The devices and the terminals can receive and perform the responsive actions. For example, before a human enters into an elevator, the sensor outside the elevator detects the human's entrance and sends that data to the UV germicidal device to change the operation state or shut down.

Figure 3:
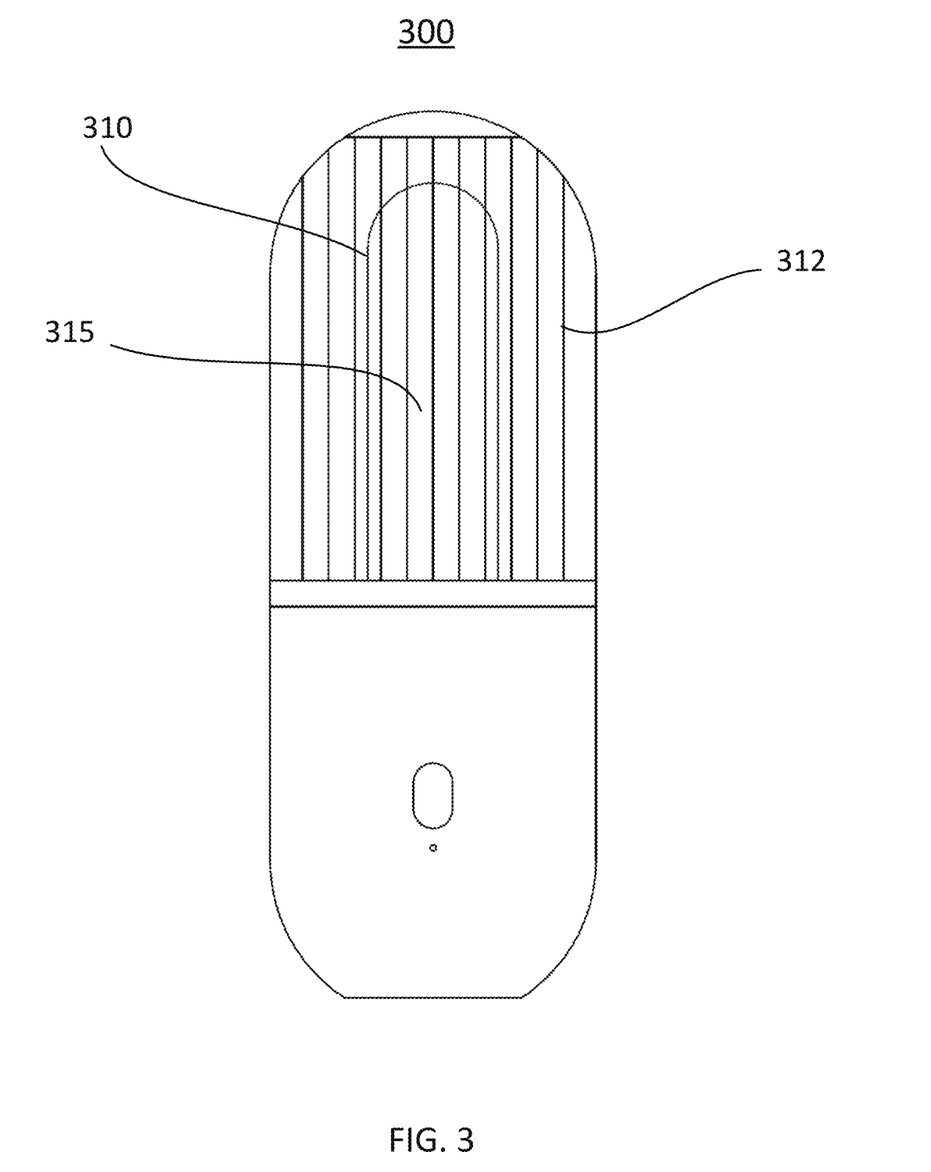
FIG. 3 shows a germicidal device according to one embodiment of the invention.
Figure 4A:
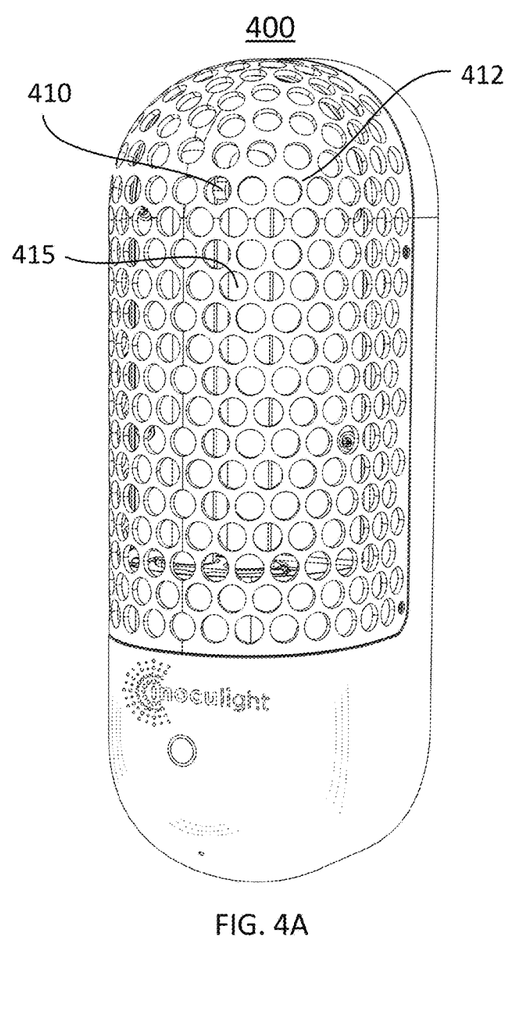
FIGS. 4A-4B show a germicidal device according to another embodiment of the invention.
Figure 4B:
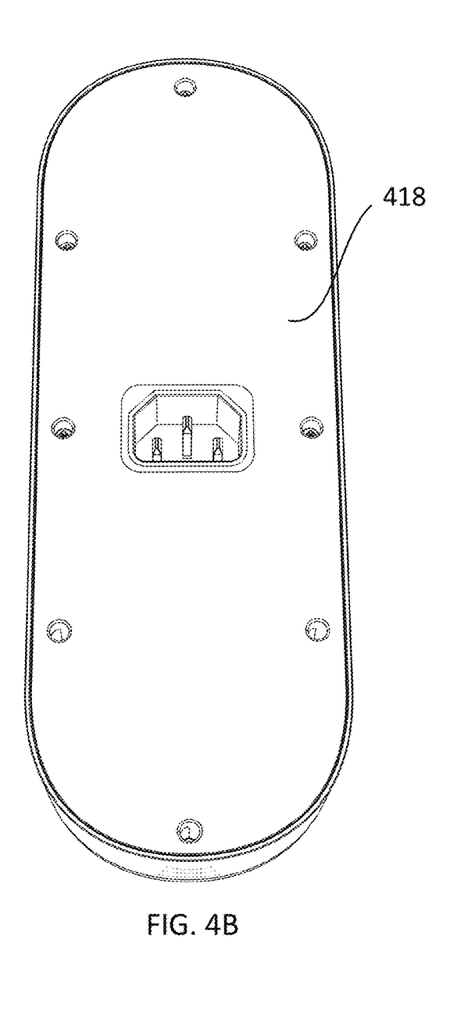

FIGS. 3 and 4A-4B show respectively germicidal devices 300 and 400 according to two different embodiments of the invention. The germicidal device 300 of FIG. 3 is a design for a stand-alone use, while the germicidal device 400 of FIGS. 4A-4B is designed to have a plat back 418 for a plug-in use. Similar to the germicidal device 100 shown in FIG. 1, each of the germicidal devices 300 and 400 includes an UV lighting member, a sensing member including built-in sensors and remote sensors, an RF receiver, a wireless networking module and an MCU. In addition, each of the germicidal devices 300 and 400 further includes a housing 312/412 surrounding the lighting member 310/410. In certain embodiments, the housing 312/412 has a plurality of openings 315/415 for allowing the UV light emitted from the lighting member 310/410 to pass through the plurality of openings 315/415 to illuminate the area.

Figure 5:
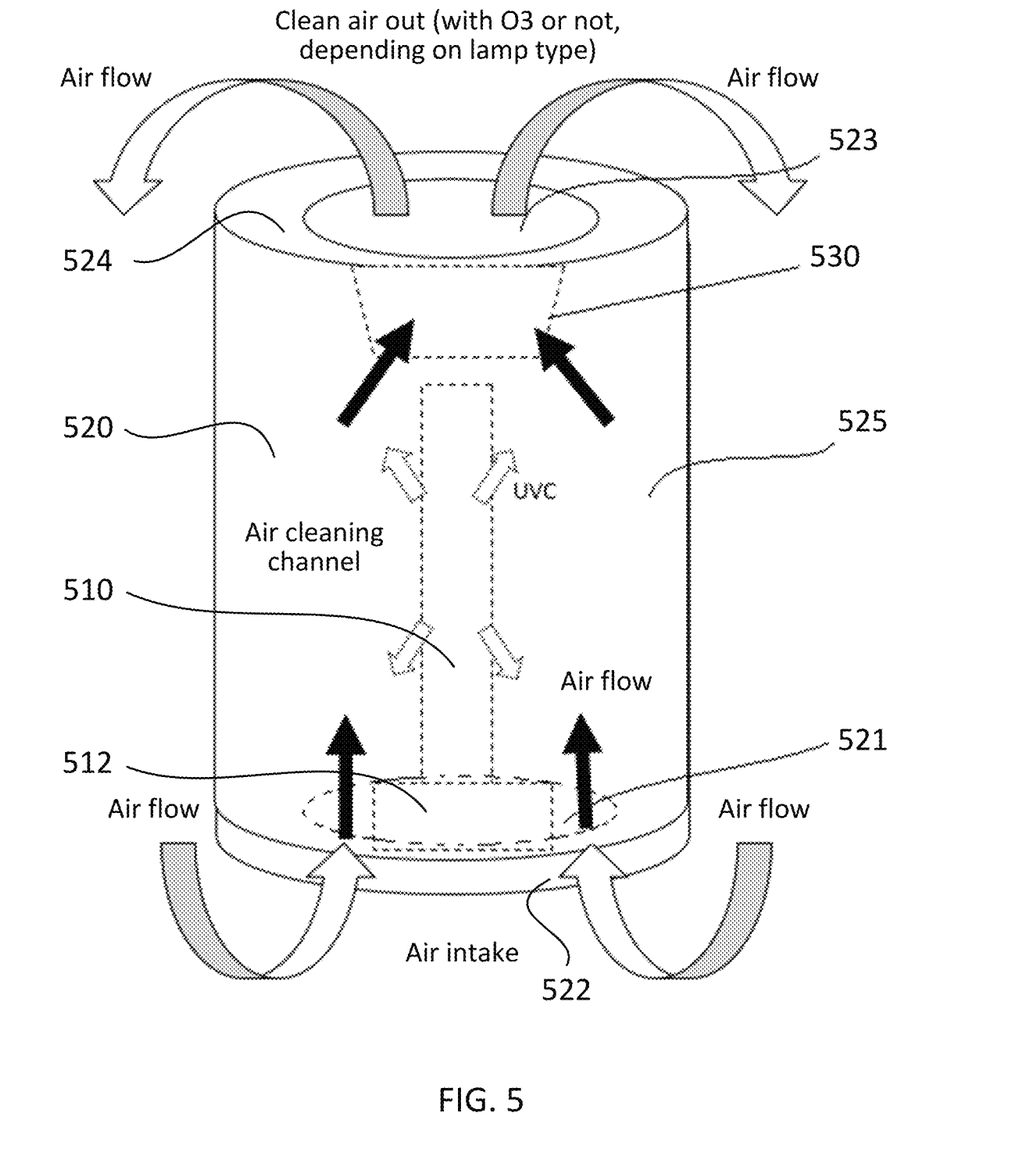
FIG. 5 shows schematically a germicidal device according to one embodiment of the invention.

In one embodiment shown in FIG. 5, the UV lamp (lighting member) 510 is placed on a lamp base 512 and surrounded by the housing 520. The housing 520 comprises at least one air inlet 521, at least one air outlet 523, and at least one air pass-through (cleaning) channel 525 defined between the at least one air inlet 521 and the at least one air outlet 523. As such, when air in the area is operably circulated through the at least one air pass-through channel 525, the UV light emitted from the UV lamp 510 kills or inactivates the microorganisms in the circulated air when it passes through the at least one air pass-through channel 525. In the exemplary embodiment shown in FIG. 5, the air inlet 521 and the air outlet 523 are respectively formed on the bottom cover 522 and the top cover 524 of the housing 520. The housing 520 is in a cylindrical form. In addition, a circulating member 530 is provided in fluid communication with the at least one air pass-through channel 525 for operably circulating the air through the at least one air pass-through channel 525. In one embodiment, the circulating member 530 comprises air blower or fan.

In the exemplary embodiment shown in FIG. 5, the UVC light emitted from the UV lamp 510 can illuminate only the air cleaning channel 525 very nearby, which makes the UVC power density of the air cleaning channel 525 very high which is beneficial to the air cleaning. The fan 530 pushes or pulls the room space air from the air inlet 521 into the air cleaning channel 525 and illuminate the same with the UVC light to kill germs and viruses in the air and then blows out the clean air into the room from the air outlet 523. If an ozone type of the UVC lamp is used, it can emit the 185 nm UV. When the air go through the UVC air cleaning channel, the air output from the air outlet 523 contains ozone. The ozone air has strong ability to kill the germs/viruses even in the blind/dead spots/corners where the UVC light cannot reach. If an ozone-free type lamp was used, the air output from the air outlet 523 contains only the clean air with no ozone.

It should be appreciated that the air inlet and the air outlet can also be formed in other portions of the housing. The housing can also formed in other forms. Additionally, depending on the type of the circulating member 530, the ports 521 and 523 can function as the air inlet 521 and the air outlet 523, respectively, as shown in FIG. 5, or the air outlet and the air inlet, respectively.

Figure 6:
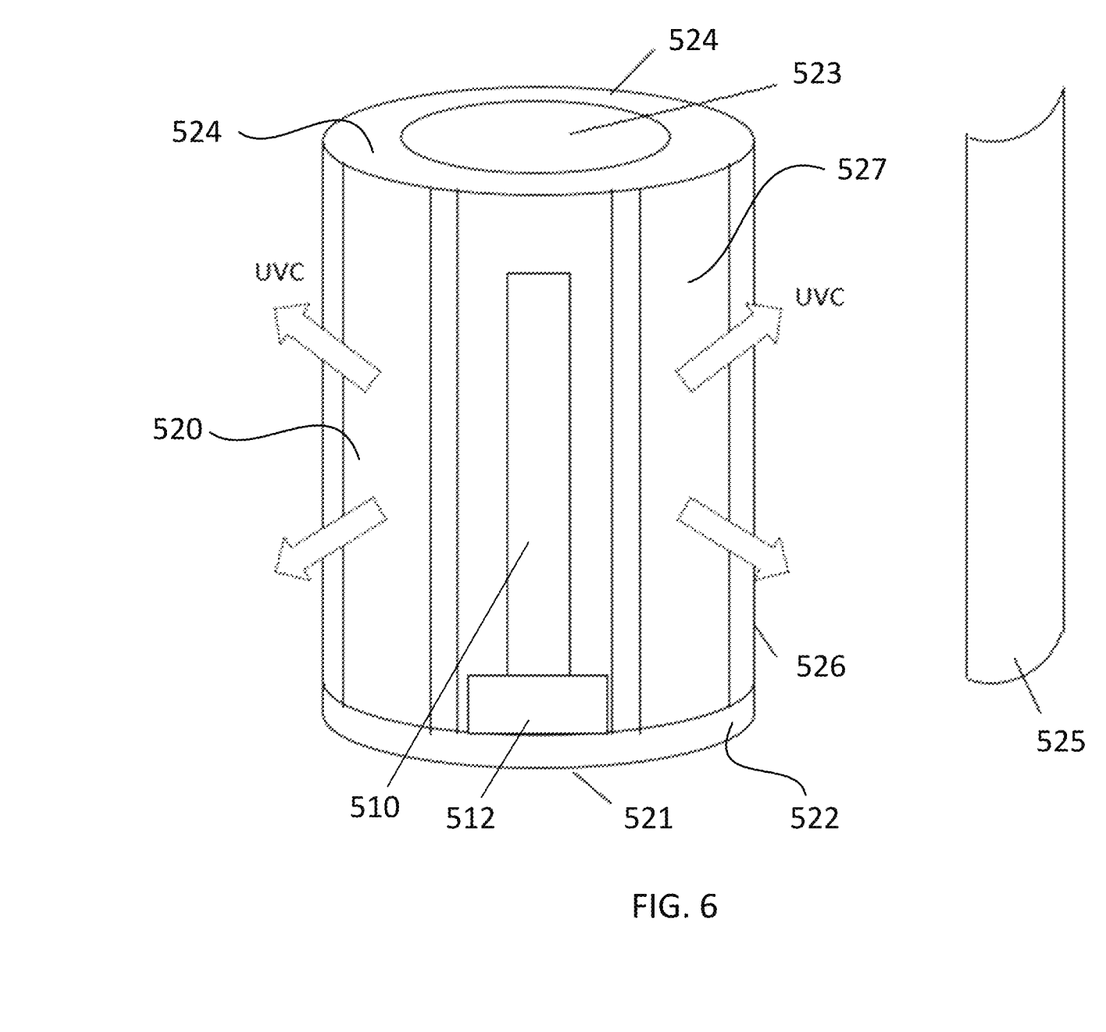
FIG. 6 shows schematically a germicidal device according to another embodiment of the invention.

In certain embodiments, as shown in FIG. 6, the housing 520 is formed with a plurality of shutter boards 525 that are movably and/or detachably jointed to each other. as shown in FIG. 6, when the shutter boards 525 are manually or automatically disassembled so that the housing 520 has only base support structures including the bottom cover 521, the top cover 523, and a plurality of pillars/columns 526 to define a plurality of windows 527 for allowing the UV light emitted from the UV lamp 510 to pass through the plurality of windows 527 to illuminate the area, the germicidal device can operates in an illuminating mode to kill or inactivate the microorganisms in the illuminated area. When the shutter boards 525 are manually or automatically assembled together to cover the UV lamp 510 as shown in FIG. 5, the germicidal device can operates in an air sterilizer mode for circulating the air through the at least one air pass-through channel 525, so as to kill or inactivate the microorganisms in the circulated air.

In certain embodiments, the germicidal device is configured to selectively operate in an illuminating mode, or in an air sterilizer mode. When the germicidal device operates in an illuminating mode, the shutter boards are moved to define a plurality of windows for allowing the UV light emitted from the lighting member to pass through the plurality of windows to illuminate the area. When the germicidal device operates in an air sterilizer mode, the shutter boards are moved to close the plurality of windows for circulating the air through the at least one air pass-through channel. In operation, when an event such as the human or animal presence is detected, the MCU can shut down the whole device, or control to close the shutter boards 525 and switch the germicidal device from the illuminating mode to the air sterilization mode that encapsulates the UV lamp 510 inside of the housing 520 so that the device keeps working to clean the surrounding air, which can be used for various environments such as an elevator.

As well known, SARS-CoV-2 virus is sensitive to UV light. Based upon this feature, the germicidal device can be used to kill the virus by emitting the UV light at a wavelength of about 185 nm, 222 nm and 253.7 nm. The germicidal device also incorporates a smart broad-contact sensing, Bluetooth® remote (smartphone) control. The germicidal device can be used in home, car, as well as public places, such as elevators, public toilets, kitchens, classrooms, student dormitories, hotel rooms, restaurant clubs, entertainment venues, and to sanitize mobile phones, small appliances, etc. The germicidal device can be used to kill viruses and other pathogens effectively in daily environment, preventing virus contact thus halting disease transmission.

In certain embodiments, the germicidal device is a portable device including a portable sterilizer with body sensing and remote control functions for disinfection of homes, dormitories, classrooms, corridors, cars, mobile phones and small electrical appliances, and so on.

In certain embodiments, the germicidal device is a mini device including a smart sterilizer with body sensing and remote control functions for disinfection of elevators, restaurants and other public places.

In certain embodiments, technical characteristics of the germicidal device include, but is not limited to: high power UVC 185 nm, 222 nm and 253.7 nm light source; compatible with wide voltages (110-240V, 3.3-18V), standard and USB power connector, built-in battery (optional); various installation methods such as wall plugs, paste installation, ceiling installation; human sensor and timing control; Bluetooth® and/or Wi-Fi wireless network and cloud storage; and various sizes: portable—palm size; mini—orange size.

In certain embodiment, operations of the germicidal device include, but is not limited to (1) simply plugging the germicidal device in an outlet of an area (e.g., room, elevator, hallway, etc.) to be sterilized, or charging the battery and placing the germicidal device in an area where a user wants to operate in; (2) remote controllable through user's mobile phone—timing on and off, repeating and reminder; and (3) human sensing: automatically turning on the light after people left, as well as automatically turning off the light after people in.

In certain embodiments, a plurality of germicidal devices can be installed in different places/rooms to construct a germicidal device network for disinfection of the different places/rooms simultaneously, sequentially or individually. The plurality of germicidal devices can be individually or cooperatively controlled, either manually or remotely.

Figure 7:
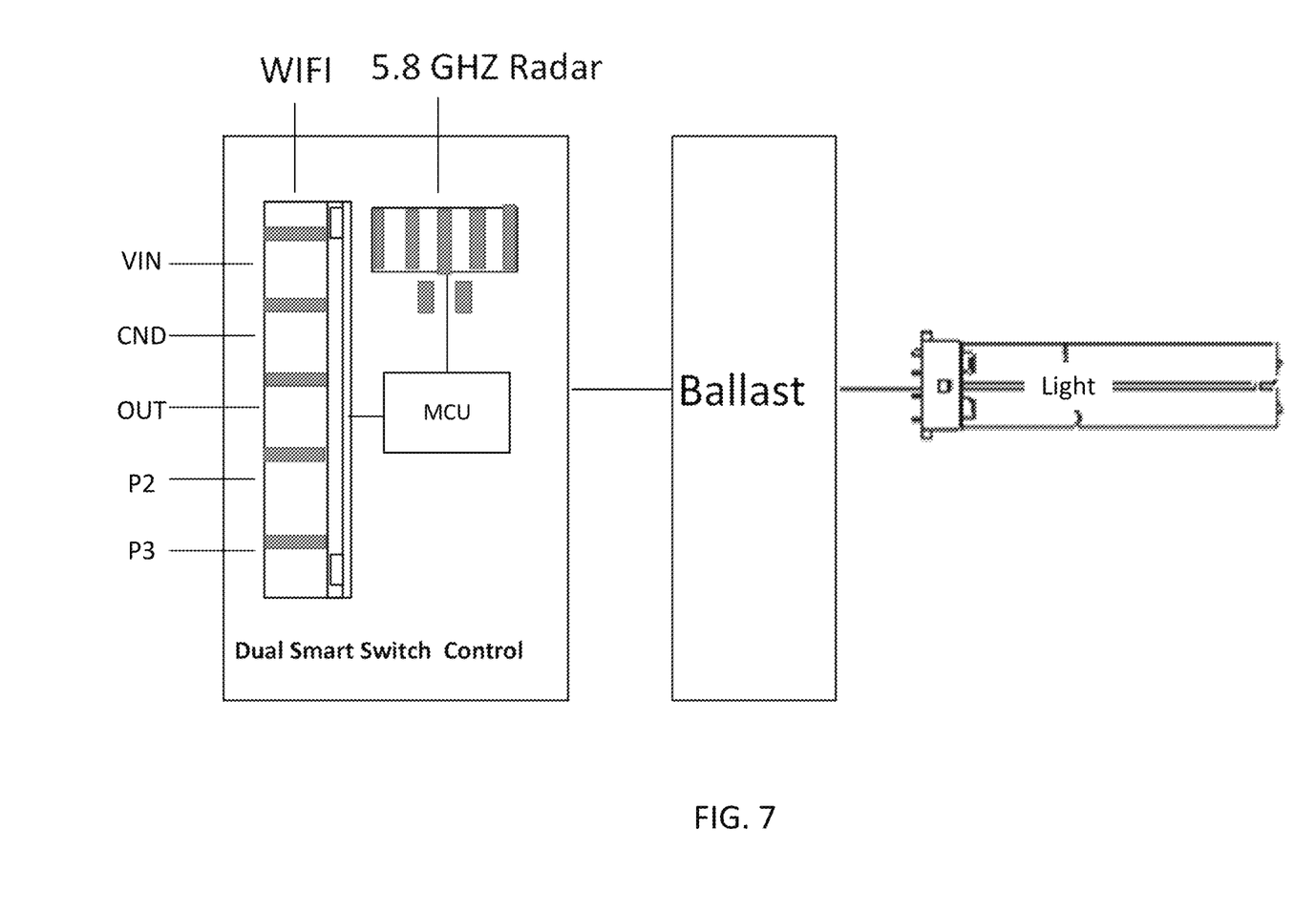
FIG. 7 shows a dual smart switch control PCB module according to one embodiment of the invention.

FIG. 7 shows a dual smart switch control PCB module according to one embodiment of the invention. The dual smart switch control PCB module is formed in a mini dual intelligent light switch mobile phone control chip including, but is not limited to, a Wi-Fi module and a 5.8 GHz radar. The dual smart switch control is coupled to the light member via a ballast to control the operation of the light member. In one embodiment, the chip specifications are as follows:

UV Wavelength: Dual UVC Wavelength,
Input Voltage: 110V or 240V,
Input Power: 10 W-200 W,
Input Frequency: 50/60 Hz,
Working Current: 110 v/160 mA/240V/80 mA,
Operation Control: APP Remote Control,
Dynamic Sensor: Automatically turn off the light when people or pets are detected, and automatically turn on the light after people or pets leave.

Figure 8:
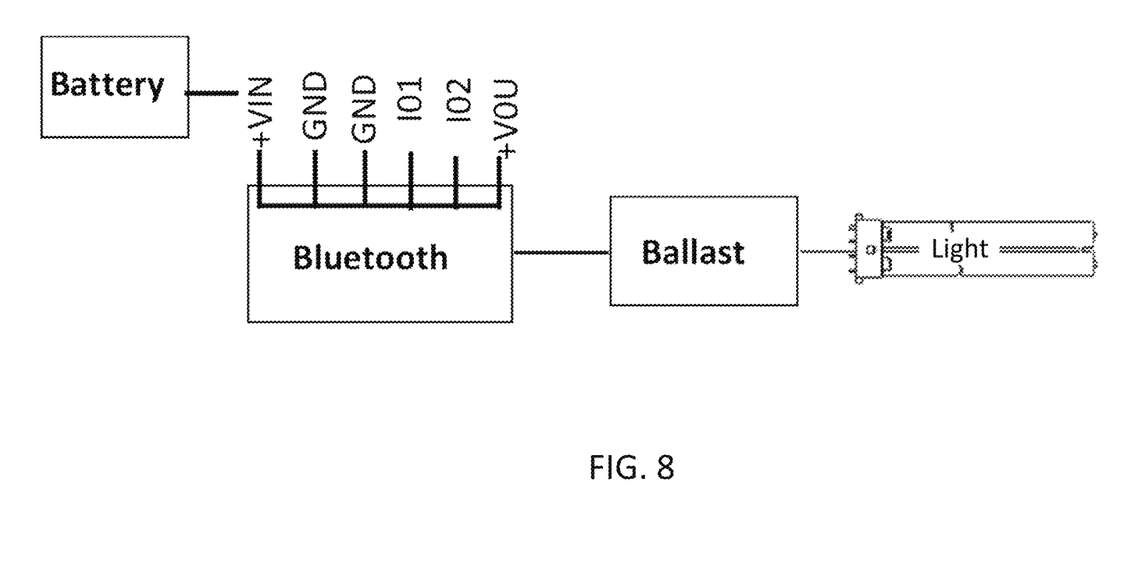
FIG. 8 shows a low-power Bluetooth® switch control module according to one embodiment of the invention.

FIG. 8 shows a low-power Bluetooth® switch control module according to one embodiment of the invention. The low-power Bluetooth® switch control module is coupled to the light member via a ballast to control the operation of the light member. In one embodiment, the module specifications are as follows:

Input Voltage: 3.3-18V,
Input Power: 3 W-10 W,
Input Frequency: DC,
Working Current: 0.6 A,
Operation Control: APP Remote Control,
Battery Capacity: 1000 mAh (with certification),
Charging time: About 2 hours in full.

Another aspect of the invention provides a method for killing microorganisms in an area with the germicidal device as disclosed above. In some embodiments, the method comprises detecting, by the sensing member, at least one event occurred in the area; and operating, by the MCU, the lighting member in a respective state in accordance with the detected at least one event occurred in the area. The at least one event includes a movement in the area, an acoustic wave in the area, an intrusion into the area, an expiration of an on-state time period in which the lighting member is in the on-state, an expiration of an off-state time period in which the lighting member is in the off-state, and/or an instruction from a remote operation.

In one embodiment, the operating step comprises, when the lighting member is in the on-state, switching the lighting member from the on-state to the off-state if one of a movement in the area, an expiration of the on-state time period and a remote instruction to turn off the lighting member is detected.

In one embodiment, the operating step comprises, when the lighting member is in the off-state, switching the lighting member from the off-state to the on-state if an expiration of the off-state time period or a remote instruction to turn on the lighting member is detected.

In one embodiment, the method further comprises selectively operating the germicidal device in an illuminating mode in which the germicidal device is adapted such that the emitted UV light directly illuminates the area so as to kill the microorganisms in the illuminated area, or in an air sterilizer mode in which the germicidal device is adapted such that air in the area is circulated to pass through the emitted UV light so as to kill the microorganisms in the circulated air.

It should be noted that all or a part of the steps according to the embodiments of the present invention is implemented by hardware or a program instructing relevant hardware. Yet another aspect of the invention provides a non-transitory tangible computer-readable medium storing instructions which, when executed by one or more processors, cause a germicidal device to perform the above-disclosed method for killing microorganisms in an area. The computer executable instructions or program codes enable a computer or a similar computing system to complete various operations in the above disclosed method for privilege management. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

According to this invention, the germicidal device, among other things, has at least the following advantages.

The UVC technology mimics the sun light to kill or inactivate germs from living environments. The germicidal device has strong disinfection performance. Combined with intelligent control technology, it can kill pathogens in the environment while protecting humans from damages of exposure of UV and UV derivatives.

Easy to use: Small size and easy to use. The combination of intelligent AI technology and sensor network technology ensures the perception of people flow characteristics and intelligent disinfection during idle time.

Simple apply: Through the intelligent adaptive functions, the germicidal device can be automatically applied to different scenarios and has a wide range of applications.

Cost-effective: Cost optimization through tools such as value engineering, products are cheap and easy to promote.

Applications of the invention: This invention introduces a new portable UVC germicidal device—Inoculight™. This device combines smart technology/space/surface and air sterilization functions with or without ozone. It can be used in indoor such as home including foyer, corridor, bedroom, living room, shoe cabinet, kitchen and restrooms, dormitories, classrooms, offices, restaurants, hotels, entertainment venues, etc., elevators, cars, small devices such as mobile phones, iPad, tablets, etc., household appliances such as refrigerators, washing machines, etc., furniture such as wardrobes, and food, etc., other public places, and so on.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A germicidal device, comprising:
   a lighting member operably in an on-state in which the lighting member emits ultraviolet (UV) light for killing microorganisms in an area, or in an off-state in which the lighting member emits no light, wherein the lighting member comprises a light source for emitting the UV light having a wavelength of 185 nm, wherein the light source comprises one or more UV light-emitting diodes (LEDs), and a low-pressure mercury lamp, and wherein the microorganisms include bacteria, fungi, viruses and/or spores;
   a sensing member configured to detect a movement in the area, an acoustic wave in the area, an intrusion into the area, an expiration of an on-state time period in which the lighting member is in the on-state, an expiration of an off-state time period in which the lighting member is in the off-state, and an instruction from a remote operation, wherein the sensing member comprises a built-in sensor unit comprising at least one motion sensor, at least one acoustic sensor and at least one timer, and a remote sensor unit consisting of a photo eye system and/or an electric fencing system, wherein the electric fencing system is configured to detect the intrusion into the area when a person or animal approaches to an invisible electric fence that is generated by the electric fencing system and surrounds the germicidal device, and wherein the photo eye system is configured to detect the intrusion into the area when the person or animal approaches to an invisible infrared fence that is generated by the photo eye system and surrounds the germicidal device; and a microcontroller unit (MCU) coupled with the lighting member and the sensing member, wherein the MCU is configured to control operations of the lighting member in a respective state in accordance with a detection of the sensing member in the area, such that when the lighting member is in the on-state and the sensing member detects an intrusion of the person or animal into the area, the MCU immediately switches the lighting member from the on-state to the off-state, wherein the lighting member, the built-in sensor unit and the MCU are assembled in a single unit.

2. The germicidal device of claim 1, being configured to operate in one of:

a default operation mode in which the lighting member is automatically in the on-state when a time is in the on-state time period, or in the off-state when the time is in the off-state time period, wherein the on-state time period and the off-state time period are predetermined;

a manual operation mode having an on-operation and an off-operation, wherein the on-operation causes the lighting member to be in the on-state, and the off-operation causes the lighting member to be in the off-state; and a remote operation mode in which the lighting member is operably in one of the on-state and the off-state in response to operations of a remote control or executions of an app of a mobile device.

3. The germicidal device of claim 2, being configured such that when the lighting member is in the on-state and the sensing member detects an expiration of the on-state time period or a remote instruction to turn off the lighting member, the MCU switches the lighting member from the on-state to the off-state; or when the lighting member is in the off-state and the sensing member detects an expiration of the off-state time period or a remote instruction to turn on the lighting member, the MCU switches the lighting member from the off-state to the on-state.

4. The germicidal device of claim 1, wherein the UV light further has a wavelength of 222 nm, or 253.7 nm.

5. The germicidal device of claim 1, wherein the built-in sensor unit further comprises at least one radar sensor for detecting a moving or stationary object in the area, and/or at least one temperature sensor for detecting temperature and/or temperature change of the area.

6. The germicidal device of claim 1, wherein the at least one motion sensor comprises one or more microwave sensors, and/or one or more passive infrared (PIR) sensors.

7. The germicidal device of claim 5, wherein the built-in sensor unit further comprises a radio frequency (RF) receiver coupled with the MCU for operably detecting the instruction from the remote operation of a remote control, and/or a wireless networking module coupled with the MCU for operably detecting the instruction from the remote operation of an app of the mobile device.

8. The germicidal device of claim 7, wherein the wireless networking module comprises a Wi-Fi module.

9. The germicidal device of claim 1, further comprising a power module for providing power to the lighting member, the sensing member and the MCU.

10. The germicidal device of claim 1, further comprising a housing surrounding the lighting member.

11. The germicidal device of claim 10, wherein the housing has a plurality of openings for allowing the UV light emitted from the lighting member to pass through the plurality of openings to illuminate the area.

12. The germicidal device of claim 10, wherein the housing comprises at least one air inlet, at least one air outlet, and at least one air pass-through channel defined between the at least one air inlet and the at least one air outlet, such that when air in the area is operably circulated through the at least one air pass-through channel, the UV light emitted from the light member kills the microorganisms in the circulated air.

13. The germicidal device of claim 12, further comprising a circulating member in fluid communication with the at least one air pass-through channel for operably circulating the air through the at least one air pass-through channel.

14. The germicidal device of claim 13, wherein the circulating member comprises one or more fans.

15. The germicidal device of claim 13, wherein the housing is formed with a plurality of shutter boards that are movably jointed to each other.

16. The germicidal device of claim 15, being configured to selectively operate in an illuminating mode, or in an air sterilizer mode, wherein when the germicidal device operates in an illuminating mode, the shutter boards are moved to define a plurality of windows for allowing the UV light emitted from the lighting member to pass through the plurality of windows to illuminate the area; and when the germicidal device operates in an air sterilizer mode, the shutter boards are moved to close the plurality of windows for circulating the air through the at least one air pass-through channel.

17. A germicidal device, comprising:

a lighting member operably in an on-state in which the lighting member emits ultraviolet (UV) light for killing microorganisms in an area, or in an off-state in which the lighting member emits no light, wherein the lighting member comprises a light source for emitting the UV light;

a sensing member comprising a built-in sensor unit comprising at least one motion sensor, at least one acoustic sensor and at least one timer for timing, and a remote sensor unit consisting of a photo eye system and/or an electric fencing system, wherein the electric fencing system is configured to detect the intrusion into the area when a person or animal approaches to an invisible electric fence that is generated by the electric fencing system and surrounds the germicidal device, and wherein the photo eye system is configured to detect the intrusion into the area when the person or animal approaches to an invisible infrared fence that is generated by the photo eye system and surrounds the germicidal device; and a microcontroller unit (MCU) coupled with the lighting member and the sensing member, wherein the MCU is configured to control operations of the lighting member in a respective state in accordance with a detection of the sensing member in the area, such that when the lighting member is in the on-state and the sensing member detects an intrusion of the person or animal into the area, the MCU immediately switches the lighting member from the on-state to the off-state, wherein the lighting member, the built-in sensor unit and the MCU are assembled in a single unit.

18. The germicidal device of claim 17, wherein the sensing member further comprises a wireless networking module coupled with the MCU for operably detecting the instruction from the remote operation of an app of a mobile device.

* * * * *